United States Patent
Ip et al.

(10) Patent No.: US 11,607,403 B2
(45) Date of Patent: Mar. 21, 2023

(54) METHODS AND COMPOSITIONS FOR PROMOTING ADULT NEUROGENESIS

(71) Applicant: Morningside Ventures Limited, Hong Kong (CN)

(72) Inventors: Nancy Yuk-Yu Ip, Hong Kong (CN); Wing-Yu Fu, Hong Kong (CN); Fanny Chui Fun Ip, Hong Kong (CN); Kit Yu Fu, Hong Kong (CN)

(73) Assignee: Morningside Ventures Limited, Hong Kong (CN)

( * ) Notice: Subject to any disclaimer, the term of this patent is extended or adjusted under 35 U.S.C. 154(b) by 40 days.

(21) Appl. No.: 15/774,456

(22) PCT Filed: Nov. 8, 2016

(86) PCT No.: PCT/IB2016/056723
§ 371 (c)(1),
(2) Date: May 8, 2018

(87) PCT Pub. No.: WO2017/081609
PCT Pub. Date: May 18, 2017

(65) Prior Publication Data
US 2019/0247366 A1    Aug. 15, 2019

Related U.S. Application Data

(60) Provisional application No. 62/252,952, filed on Nov. 9, 2015.

(51) Int. Cl.
*A61K 31/426* (2006.01)
*A61K 45/06* (2006.01)
(Continued)

(52) U.S. Cl.
CPC .......... *A61K 31/426* (2013.01); *A61K 45/06* (2013.01); *A61P 25/16* (2018.01); *A61P 25/22* (2018.01);
(Continued)

(58) Field of Classification Search
CPC .. A61K 31/426; A61K 2300/00; A61K 45/06; A61P 25/24; A61P 25/28;
(Continued)

(56) References Cited

U.S. PATENT DOCUMENTS 4,522,811 A     6/1985  Eppstein et al.
9,134,327 B2 *  9/2015  Ip ...................... G01N 33/6896
                         (Continued)

FOREIGN PATENT DOCUMENTS

CN    102112879       6/2011
CN    103893131 A     7/2014
                (Continued)

OTHER PUBLICATIONS

Wiley-Blackwell. "Gout and Parkinson's: Studies Examine Treatment For Gout and the Condition's Protective Effects." ScienceDaily. ScienceDaily, Nov. 8, 2008. <www.sciencedaily.com/releases/2008/11/081104132923.htm>.*

(Continued)

*Primary Examiner* — Savitha M Rao
(74) *Attorney, Agent, or Firm* — Foley & Lardner LLP (57) ABSTRACT

The therapeutic uses of febuxostat or febuxostat derivatives and compositions comprising febuxostat or febuxostat derivatives to promote neurogenesis for the treatment of disease.

6 Claims, 6 Drawing Sheets

(51) Int. Cl.
    *A61P 25/28* (2006.01)
    *A61P 25/22* (2006.01)
    *A61P 25/24* (2006.01)
    *A61P 27/16* (2006.01)
    *A61P 25/16* (2006.01)

(52) U.S. Cl.
    CPC .............. *A61P 25/24* (2018.01); *A61P 25/28* (2018.01); *A61P 27/16* (2018.01)

(58) Field of Classification Search
    CPC .......... A61P 25/16; A61P 25/22; A61P 27/16; A61P 25/22
    USPC ........................................................ 514/365
    See application file for complete search history.

(56) References Cited

U.S. PATENT DOCUMENTS

| | | | |
|---|---|---|---|
| 9,629,830 B2 * | 4/2017 | Ip | A61P 25/24 |
| 2010/0010054 A1 | 1/2010 | Nishino et al. | |
| 2014/0249318 A1 | 9/2014 | Nakatsuji et al. | |
| 2018/0142287 A1 * | 5/2018 | Chu Ip | C12Q 1/6883 |

FOREIGN PATENT DOCUMENTS

| | | |
|---|---|---|
| WO | WO-2012/037093 | 3/2012 |
| WO | WO-2015/007222 A1 | 1/2015 |

OTHER PUBLICATIONS

Schumacher HR Jr, ( Effects of febuxostat versus allopurinol and placebo in reducing serum urate in subjects with hyperuricemia and gout: a 28-week, phase III, randomized, double-blind, parallel-group trial. Arthritis Rheum. 2008 N).*
Al-Khateeb et al (Journal of Alzheimer's Disease, vol. 44, No. 3, pp. 859-865, 2015, Feb. 6, 2015).*
Ming GL, Song H. Adult neurogenesis in the mammalian brain: significant answers and significant questions. Neuron. 2011;70(4):687-702. doi: 10.1016/j.neuron.2011.05.001,2011).*
Rodriguez et al. (vol. 219, Issue 1, Jul. 2011, pp. 78-89, Journal of Anatomy, Neurogenesis in Alzheimer's disease,).*
International Search Report and Written Opinion in International Application No. PCT/IB2016/056723 dated Feb. 20, 2017 (10 pages).
Shibagaki et al., "Safety, efficacy and renal effect of febuxostat in patients with moderate-to-severe kidney dysfunction," Hypertension Research, vol. 37, Jun. 19, 2014, pp. 919-925.
First Office Action in CN Patent Application No. 201680078350.7 dated Jun. 12, 2020 (with English translation) (15 pages).
Karve et al. "Evaluation of effect of allopurinol and febuxostat in behavioral model of depression in mice" Indian Journal of Pharmacology, vol. 45 Issue 3, pp. 244-247.
Shibagaki, et al. "Safety, efficacy and renal effect of febuxostat in patients with moderate-to-severe kidney dysfunction" Hypertension Research (2014) Issue 37, pp. 919-925.
Hollands et al., "Alzheimer's Disease and Hippocampal Adult Neurogenesis; Exploring Shared Mechanisms," Frontiers in Neuroscience, 2016, vol. 10, Article 178, 8 pages.

* cited by examiner

METHODS AND COMPOSITIONS FOR PROMOTING ADULT NEUROGENESIS

CROSS REFERENCE TO RELATED APPLICATIONS

This application is a U.S. National Stage Application under 35 U.S.C. § 371 of PCT/IB2016/056723, filed Nov. 8, 2016, which claims priority to U.S. provisional application 62/252,952, filed Nov. 9, 2015, which are incorporated herein by reference in their entireties.

FIELD OF TECHNOLOGY

This disclosure relates generally to therapeutic uses of febuxostat or febuxostat derivatives and compositions comprising febuxostat or febuxostat derivatives to promote neurogenesis for the treatment of disease.

INTRODUCTION

Adult neurogenesis requires birth, maturation, integration, and survival of neurons. Approximately one-third of the mammalian hippocampal region is renewed throughout life, with the addition of roughly 1,400 new neurons per day. This rate declines with advancing age, and reduced neurogenesis is associated with elevated stress, psychiatric disorders, and neurodegenerative conditions. Accordingly, agents that promote adult neurogenesis are useful for treating or alleviating the symptoms of such conditions, and for improving age-related decreases in mental function.

SUMMARY

In one aspect, the present disclosure provides methods for promoting adult neurogenesis in a subject in need thereof, comprising administering to the subject a composition comprising febuxostat or a febuxostat derivative. In some embodiments, the subject is suspected or diagnosed as having a psychiatric disorder, noise-induced hearing loss, age-related neuron loss, tardive dyskinesia, or a neurodegenerative condition. In some embodiments, the psychiatric disorder is selected from the group consisting of anxiety and depression. In some embodiments, the neurodegenerative condition is selected from the group consisting of Alzheimer's Disease (AD), Parkinson's Disease (PD), and amyotrophic lateral sclerosis (ALS). In some embodiments, the febuxostat or febuxostat derivative promotes neuronal progenitor amplification. In some embodiments, the febuxostat or febuxostat derivative promotes neuronal differentiation. In some embodiments, the febuxostat or febuxostat derivative promotes an increase in the number of doublecortin-positive ($DCX^+$) cells in the subject's hippocampal region. In some embodiments, the method further comprises administering one or more additional agents for promoting adult neurogenesis.

In one aspect, the present disclosure provides methods for treating a psychiatric disorder in a subject in need thereof, comprising administering to the subject a composition comprising febuxostat or a febuxostat derivative. In some embodiments, the psychiatric disorder is selected from the group consisting of anxiety and depression. In some embodiments, the febuxostat or febuxostat derivative promotes neuronal progenitor amplification. In some embodiments, the febuxostat or febuxostat derivative promotes neuronal differentiation. In some embodiments, the febuxostat or febuxostat derivative promotes an increase in the number of doublecortin-positive ($DCX^+$) cells in the subject's hippocampal region. In some embodiments, the method further comprises administering one or more additional agents for treatment of the psychiatric disorder.

In one aspect, the present disclosure provides methods for treating a neurodegenerative condition in a subject in need thereof, comprising administering to the subject a composition comprising febuxostat or a febuxostat derivative. In some embodiments, the neurodegenerative condition is selected from the group consisting of Alzheimer's Disease (AD), Parkinson's Disease (PD), and amyotrophic lateral sclerosis (ALS). In some embodiments, the febuxostat or febuxostat derivative promotes neuronal progenitor amplification. In some embodiments, the febuxostat or febuxostat derivative promotes neuronal differentiation. In some embodiments, the febuxostat or febuxostat derivative promotes an increase in the number of doublecortin-positive ($DCX^+$) cells in the subject's hippocampal region. In some embodiments, the method further comprises administering one or more additional agents for treatment of the neurodegenerative condition.

In one aspect, the present disclosure provides methods for treating noise-induced hearing loss in a subject in need thereof, comprising administering to the subject a composition comprising febuxostat or a febuxostat derivative. In some embodiments, the febuxostat or febuxostat derivative promotes neuronal progenitor amplification. In some embodiments, the febuxostat or febuxostat derivative promotes neuronal differentiation. In some embodiments, the febuxostat or febuxostat derivative promotes an increase in the number of doublecortin-positive ($DCX^+$) cells in the subject's hippocampal region. In some embodiments, the method further comprises administering one or more additional agents for the treatment of noise-induced hearing loss.

In one aspect, the present disclosure provides methods for treating tardive dyskinesia in a subject in need thereof, comprising administering to the subject a composition comprising febuxostat or a febuxostat derivative. In some embodiments, the administration of febuxostat or febuxostat derivative promotes neuronal progenitor amplification. In some embodiments, the febuxostat or febuxostat derivative promotes neuronal differentiation. In some embodiments, the febuxostat or febuxostat derivative promotes an increase in the number of doublecortin-positive ($DCX^+$) cells in the subject's hippocampal region. In some embodiments, the method further comprises administering one or more additional agents for the treatment of tardive dyskinesia.

BRIEF DESCRIPTION OF THE FIGURES

The figures included herein depict non-limiting exemplary embodiments of the technology disclosed herein and are provided to aid the reader in understanding the disclosure.

DETAILED DESCRIPTION

I. General

The present disclosure provides methods and compositions comprising febuxostat for promoting adult neurogenesis. It is to be appreciated that certain aspects, modes, embodiments, variations and features of the technology disclosed herein are described below in various levels of detail in order to provide a substantial understanding technology.

Unless defined otherwise, all technical and scientific terms used herein generally have the same meaning as commonly understood by one of ordinary skill in the art to which this technology belongs. As used in this specification and the appended claims, the singular forms "a," "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art. Standard techniques are used for nucleic acid and peptide synthesis. Standard techniques, or modifications thereof, are used for chemical syntheses and chemical analyses. All references cited herein are incorporated herein by reference in their entireties and for all purposes to the same extent as if each individual publication, patent, or patent application was specifically and individually incorporated by reference in its entirety for all purposes.

As used herein, "febuxostat" and refers to 2-(3-cyano-4-isobutoxyphenyl)-4-methyl-1,3-thiazole-5-carboxylic acid (IUPAC), also known as 2-[3-cyano-4-(2-metylpropoxy)phenyl]-4-metyltiazole-5-carboxylic acid (WHO) and 5-tiazolecarboxylic acid, 2-[3-cyano-4-(2-metylpropoxy)phenyl]-4-methyl-(USAN). Febuxostat derivatives include compounds modified to improve some aspect of the agent, such as, for example, potency, stability, or half life. The term encompasses febuxostat derivatives for which the modification accomplished the intended effect, as well as those for which the intended effect was not accomplished. As used herein, the term "febuxostat derivatives" likewise encompasses modified compounds for which no improvement was intended or accomplished.

As used herein, "derivatives" or "analogs" of febuxostat include, but are not limited to, compounds that are structurally similar to the febuxostat or in the same general chemical class as febuxostat. In some embodiments, the derivative or analog of febuxostat retains similar chemical and/or physical property (including, for example, functionality) of the therapeutic agent or moiety. In some embodiments, the derivative or analog of febuxostat displays improved properties as compared to febuxostat, such as increased stability or plasma half-life.

As used herein, the term "febuxostat" also encompasses trade and generic references to the compound, including, but not limited to, TEI-6720, TMX-67, UNII-101V0R1N2E, ADENURIC™, ATENURIX™, BARIF™, FABUZEST™, FEBUMIN™, FEBUNEX™, FEBURIC™, FEBUS™, FEBUSTAT™, FEBUWEL™, FEBUX™, FEBUXTAT™, FELURIC™, FOSTAT™, FOXSTAT™, GOUSTAT™, GOTURIC™, ULORIC™, URISTAT™, and UROSTAT™.

As used herein, the administration of an agent or drug to a subject includes self-administration and the administration by another. It is also to be appreciated that the various modes of treatment or prevention of medical conditions as described are intended to mean "substantial," which includes total but also less than total treatment or prevention, and wherein some biologically or medically relevant result is achieved.

As used herein, the term "biological sample" means sample material derived from or contacted by living cells. The term "biological sample" is intended to include tissues, cells and biological fluids isolated from a subject, as well as tissues, cells and fluids present within a subject. Biological samples of the present technology include, e.g., but are not limited to, whole blood, plasma, semen, saliva, tears, urine, fecal material, sweat, buccal, skin, cerebrospinal fluid, and hair. Biological samples can also be obtained from biopsies of internal organs or from tissues.

As used herein, the term "effective amount" of a composition, is a quantity sufficient to achieve a desired therapeutic and/or prophylactic effect, e.g., an amount which results in the prevention of, or a decrease in, the symptoms associated with a disease that is being treated, e.g., the diseases associated with target polypeptide. The amount of a composition of the present technology administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present technology can also be administered in combination with each other, or with one or more additional therapeutic compounds.

As used herein, "expression" includes but is not limited to one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "medical condition" includes, but is not limited to, any condition or disease manifested as one or more physical and/or psychological symptoms for which treatment and/or prevention is desirable, and includes previously and newly identified diseases and other disorders.

As used herein, the term "subject" refers to an animal, preferably a mammal, such as a human, but can also be another mammal, e.g., domestic animals (e.g., dogs, cats and the like), farm animals (e.g., cows, sheep, pigs, horses and the like) and laboratory animals (e.g., monkey, rats, mice, rabbits, guinea pigs and the like).

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration.

As used herein, the term "target cell" means any cell in a subject (e.g., a human or animal) that can be targeted by compositions of the present technology.

As used herein, the terms "treating" or "treatment" or "alleviation" refers to therapeutic treatment. A subject is successfully "treated" for a condition characterized by a need for neurogenesis where, after receiving a therapeutic amount of febuxostat, the subject shows observable and/or measurable reduction in or absence of one or more signs and symptoms of the condition. As used here, "prevention" or "preventing" a disease or condition refers to prophylactic or preventative measures, wherein the object is to prevent or slow down (lessen) the targeted pathologic condition or disorder.

II. Methods of Treatment

In one aspect, the present disclosure provides methods for promoting adult neurogenesis in a subject in need thereof, comprising administering to the subject a composition comprising febuxostat or a febuxostat derivative. In some embodiments, the subject is suspected or diagnosed as having a psychiatric disorder, noise-induced hearing loss, age-related neuron loss, tardive dyskinesia, or a neurodegenerative condition. In some embodiments, the psychiatric disorder is selected from the group consisting of anxiety and depression. In some embodiments, the neurodegenerative condition is selected from the group consisting of Alzheimer's Disease (AD), Parkinson's Disease (PD), and amyotrophic lateral sclerosis (ALS).

In one aspect, the present disclosure provides methods for treating a psychiatric disorder in a subject in need thereof, comprising administering to the subject a composition comprising febuxostat or a febuxostat derivative. In some embodiments, the psychiatric disorder is selected from the group consisting of anxiety and depression.

In one aspect, the present disclosure provides methods for treating a neurodegenerative condition in a subject in need thereof, comprising administering to the subject a composition comprising febuxostat or a febuxostat derivative. In some embodiments, the neurodegenerative condition is selected from the group consisting of Alzheimer's Disease (AD), Parkinson's Disease (PD), and amyotrophic lateral sclerosis (ALS).

In one aspect, the present disclosure provides methods for treating noise-induced hearing loss in a subject in need thereof, comprising administering to the subject a composition comprising febuxostat or a febuxostat derivative.

In one aspect, the present disclosure provides methods for treating tardive dyskinesia in a subject in need thereof, comprising administering to the subject a composition comprising febuxostat or a febuxostat derivative.

In some embodiments, the febuxostat or febuxostat derivative promotes neuronal progenitor amplification, promotes neuronal differentiation, and/or promotes an increase in the number of doublecortin-positive ($DCX^+$) cells in the subject's hippocampal region.

Efficacy of therapy may be assessed or monitored using methods known in the art and appropriate for the condition being treated, such as, for example, methods for monitoring neurogenesis or the effects of neurogenesis. Such methods may include, but are not limited to, organ or tissue biopsies or clinical assessment of one or more symptoms of the condition being treated. In some embodiments, the assessment will show an increase in adult hippocampal neuron amplification and/or differentiation. In some embodiments, the assessment will show a decrease in signs or symptoms of a psychiatric disorder such as anxiety or depression, noise-induced hearing loss, age-related neuron loss, tardive dyskinesia, or a neurodegenerative condition such as Alzheimer's Disease (AD), Parkinson's Disease (PD), and amyotrophic lateral sclerosis (ALS). In some embodiments, signs or symptoms of the condition at issue will be partially ameliorated. In some embodiments, signs or symptoms of the condition at issue will be completely ameliorated.

III. Compositions

Therapeutic agents of the present technology, such as febuxostat or febuxostat derivatives, can be incorporated into pharmaceutical compositions suitable for administration to subject in need thereof for the treatment of various conditions. The pharmaceutical compositions generally comprise the febuxostat together with a pharmaceutically-acceptable carrier in a form suitable for a particular route of administration. Pharmaceutically-acceptable carriers are determined in part by the particular composition being administered, as well as by the particular method used to administer the composition. Accordingly, there is a wide variety of suitable formulations of pharmaceutical compositions for administering the febuxostat compositions (see, e.g., *Remington's Pharmaceutical Sciences*, Mack Publishing Co., Easton, Pa. 18$^{th}$ ed., 1990). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. "Pharmaceutically-acceptable salts and esters" means salts and esters that are pharmaceutically-acceptable and have the desired pharmacological properties. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid).

Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with febuxostat or febuxostat derivatives, use thereof in the compositions is contemplated. Supplementary active compounds can also be incorporated into the compositions.

Pharmaceutical compositions of the present technology are formulated to be compatible with and intended route of administration, such as, for example, parenteral, topical, intravenous, oral, subcutaneous, intraarterial, intradermal, transdermal, rectal, intracranial, intraperitoneal, intranasal; intramuscular route, or respiratory administration.

In some embodiments, formulations are administered locally, directly in to an affected tissue. In some embodiments, formulations are administered systemically. In some embodiments, formulations are administered as a bolus. In some embodiments, formulations are administered for a time-release delivery.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfate; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating febuxostat or febuxostat derivatives in the required amount in an appropriate solvent with one or a combination of ingredients enumerated above, as required, followed by filtered sterilization. Generally, dispersions are prepared by incorporating febuxostat or febuxostat derivatives into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The agents of the present technology can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, febuxostat or febuxostat derivatives can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the agent is delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the agent is formulated into ointments, salves, gels, or creams as generally known in the art.

The agent can also be prepared as pharmaceutical compositions in the form of suppositories (e.g., with conventional suppository bases such as cocoa butter and other glycerides) or retention enemas for rectal delivery.

In one embodiment, febuxostat or febuxostat derivatives are prepared with carriers that protect the agent against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions, including liposomes, can also be used as pharmaceutically-acceptable carriers. These can be prepared according to methods known to those skilled in the art, e.g., as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of febuxostat or febuxostat derivatives calculated to produce the desired therapeutic effect in association with the required pharmaceutical carrier. The specification for the dosage unit forms of the present technology are dictated by and directly dependent on the unique characteristics of febuxostat or febuxostat derivatives and the particular therapeutic effect to be achieved, and the limitations inherent in the art of compounding febuxostat or febuxostat derivatives for the treatment of a subject.

When used in vivo for therapy, febuxostat or febuxostat derivatives are administered to the subject in effective amounts (i.e., amounts that have desired therapeutic effect). The dose and dosage regimen will depend upon the degree of disease present in the individual, and the characteristics of the particular disease in question. In some embodiments, the febuxostat or febuxostat derivative is administered repeatedly over the course of days, weeks, months, or years until the desired degree of treatment is obtained.

Typically, an effective amount of the compositions of the present technology, sufficient for achieving a therapeutic or prophylactic effect, range from about 0.000001 mg per kilogram body weight per day to about 10,000 mg per kilogram body weight per day. In some embodiments, the dosage ranges are from about 0.0001 mg per kilogram body weight per day to about 100 mg per kilogram body weight per day. In some embodiments the compositions are administered at a dosage range of from about 0.0001 to 100 mg/kg, or about 0.01 to 5 mg/kg per day. For example dosages can be 1 mg/kg body weight or 10 mg/kg body weight per day, or within the range of 1-10 mg/kg per day. In some embodiments, a single dosage of febuxostat or febuxostat derivatives ranges from 0.1-10,000 micrograms per kg body weight. In some embodiments, febuxostat or febuxostat derivatives concentrations in a carrier ranges from 0.2 to 2000 micrograms per delivered milliliter. An illustrative treatment regime entails administration once per every two weeks or once a month or once every 3 to 6 months. Intervals between single dosages can be weekly, monthly or yearly. Intervals can also be irregular as indicated by measuring blood levels of febuxostat or febuxostat derivatives in the subject.

In some methods, dosage is adjusted to achieve a plasma febuxostat or febuxostat derivative concentration, of 1-1000 µg/ml and in some methods 25-300 µg/ml. Alternatively, a formulation can be administered as a sustained release formulation, in which case less frequent administration is required. Dosage and frequency vary depending on the half-life of the febuxostat or febuxostat derivatives in the subject.

In some embodiments, an effective amount of febuxostat or febuxostat derivatives will provide therapeutic benefit without causing substantial toxicity to the subject. Toxicity of the agents can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the agents described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl, et al., In: *The Pharmacological Basis of Therapeutics*, Ch. 1 (1975).

IV. Combinatorial Therapies

In one aspect, the present disclosure provides methods comprising the use of febuxostat or febuxostat derivatives in combination with one or more additional therapeutic agents. In some embodiments, the methods comprise administering febuxostat or febuxostat derivatives to a subject in need thereof, and further administering one or more additional agents for treatment of the condition at issue. In some embodiments, the one or more additional agents promote adult neurogenesis. In some embodiments, the one or more additional agents are for the treatment of a psychiatric disorder, noise-induced hearing loss, age-related neuron loss, tardive dyskinesia, or a neurodegenerative condition. In some embodiments, the one or more additional agents are for the treatment of anxiety or depression. In some embodiments, the one or more additional agents are for the treatment of Alzheimer's Disease (AD), Parkinson's Disease (PD), and amyotrophic lateral sclerosis (ALS). In some embodiments, the one or more additional agents for the treatment of psychiatric disorders are selected from the group consisting of an anticonvulsant, an antianxiety, an antimanic, an antipsychotic, a sedative-hypnotic, a stimulant, an anti-hypertensive medication, and a selective serotonin reuptake inhibitor. In some embodiments, the one or more agents for the treatment of AD are selected from the group consisting of acetylcholine esterase inhibitors (such as donepezil, rivastigmine, and galantamine), beta- and gamma-secretase inhibitors, amyloid-beta vaccines, Cu—Zn chelators, cholesterol-lowering drugs, and non-steroidal anti-inflammatory drugs. Other agents are known to those of skill in the art.

In some embodiments, the use of the combinatorial use of febuxostat or febuxostat derivatives and additional therapeutic agents has an additive effect, meaning that the therapeutic benefit of febuxostat or febuxostat derivatives and the additional agent is additive compared to the benefit of each alone. In some embodiments, the use of the combinatorial use of febuxostat or febuxostat derivatives and additional therapeutic agents has a synergistic effect, meaning that the therapeutic benefit of febuxostat or febuxostat derivatives and the additional agent is more than additive compared to the benefit of each alone.

In some embodiments, the additive or synergistic effects of febuxostat or febuxostat derivatives and the additional agent permits the administration of a lower dose of febuxostat or febuxostat derivatives and/or the additional agent as compared to the effective dose of each when used alone.

V. Kits

Also within the scope of the present technology are kits comprising febuxostat or febuxostat derivatives for use in promoting adult neurogenesis, or treating disease associated with a need for neurogenesis. The kit may contain a formulation of febuxostat or febuxostat derivatives suitable for a particular route of administration and optionally a means for administering the formulation packaged in a suitable container. The kit can further comprise instructions for using the kit to administer the febuxostat or febuxostat derivatives.

In some embodiments, the kit comprises a formulation of febuxostat or febuxostat derivatives together with one or more additional therapeutic agents.

EXAMPLES

The following examples are presented in order to more fully illustrate the preferred embodiments of the present technology. These examples should in no way be construed as limiting the scope of the present technology, as defined by the appended claims.

Example 1: Febuxostat Promotes Neural Progenitor Amplification and Neuronal Differentiation in Mammalian Brain This example demonstrates that febuxostat promotes adult neurogenesis in mice. In particular, the example demonstrates that febuxostat promotes neural progenitor amplification and neuronal differentiation in mouse brain.

To assess the effects of febuxostat on neural progenitor amplification, febuxostat or allopurinol (1 mM) were intracerebroventricularly delivered via osmotic pump infusion (0.5 μl per hour) to mouse brains for 7 days. Control subjects received vehicle alone. BrdU was administered in four injections on day 6, and brain tissues were harvested on day 7. Neural progenitor amplification was measured by quantifying the number of BrdU-positive cells in the subgranular zone (SGZ) of hippocampal tissue sections.

To assess the effects of febuxostat on adult neurogenesis, febuxostat or allopurinol (1 mM) were delivered to mouse brains for 7 days as described above. BrdU was administered in eight injections over days 2-3. The osmotic pump was removed on day 7 and brain tissues were harvested on day 14. The hippocampal slices were subjected to immunohistochemical analysis for the detection of BrdU and doublecortin (DCx) (newly formed neuron marker) stained cells in the subgranular zone of the hippocampus.

Figure 1:
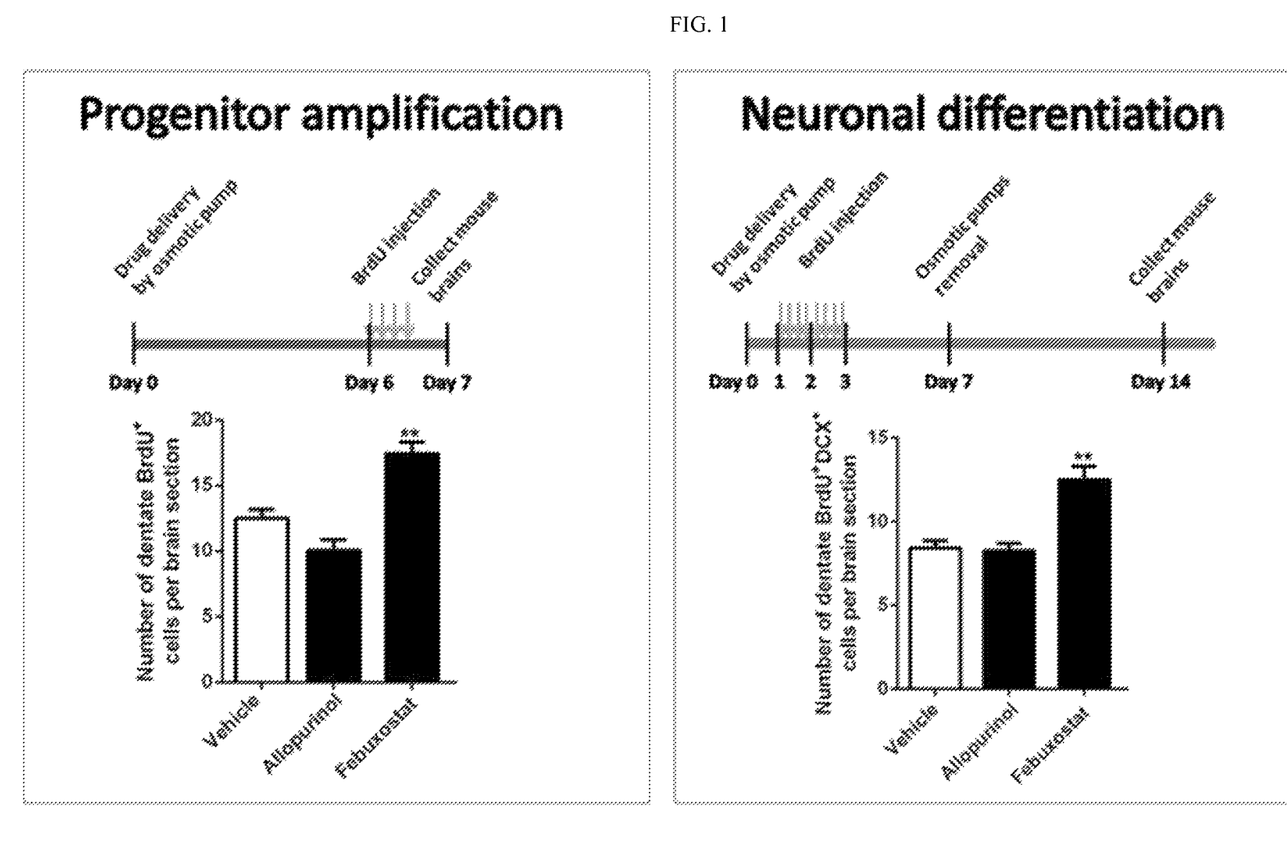
FIG. 1 is a chart showing that febuxostat promotes neural progenitor amplification and neuronal differentiation in mouse hippocampus, as compared to allopurinol and vehicle alone. Neural progenitor amplification was measured by BrdU incorporation. Neuronal differentiation was measured by doublecortin (DCX) expression in conjunction with BrdU incorporation.

Results are shown in FIG. 1. Subjects receiving febuxostat showed increased levels of neural progenitor amplification and neural differentiation compared to subjects receiving allopurinol or vehicle alone.

These results show that febuxostat is effective in methods for promoting adult neurogenesis in mammalian subjects. Accordingly, febuxostat and febuxostat derivatives are effective for the treatment of disorders characterized by reduced neurogenesis or neuron loss, such as those described herein.

Example 2: Febuxostat Promotes Neural Progenitor Amplification and Neuronal Differentiation in Mammalian Subjects Under Stress This example demonstrates that febuxostat promotes adult neurogenesis in mice under chronic stress. In particular, the example demonstrates that febuxostat promotes neural progenitor amplification and neuronal differentiation in mice subjected to chronic restraint stress (CRS).

Figure 2:
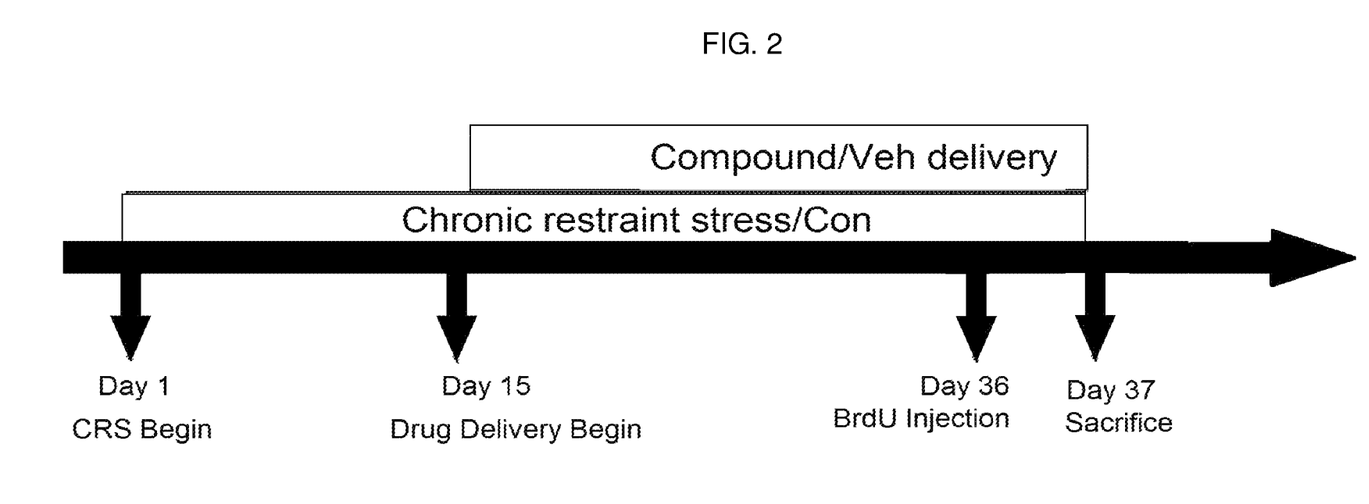
FIG. 2 is a chart showing the design of a 37-day trial to assess the effects of febuxostat on adult neurogenesis in the hippocampus of mice subjected to chronic restraint stress.
Figure 4:
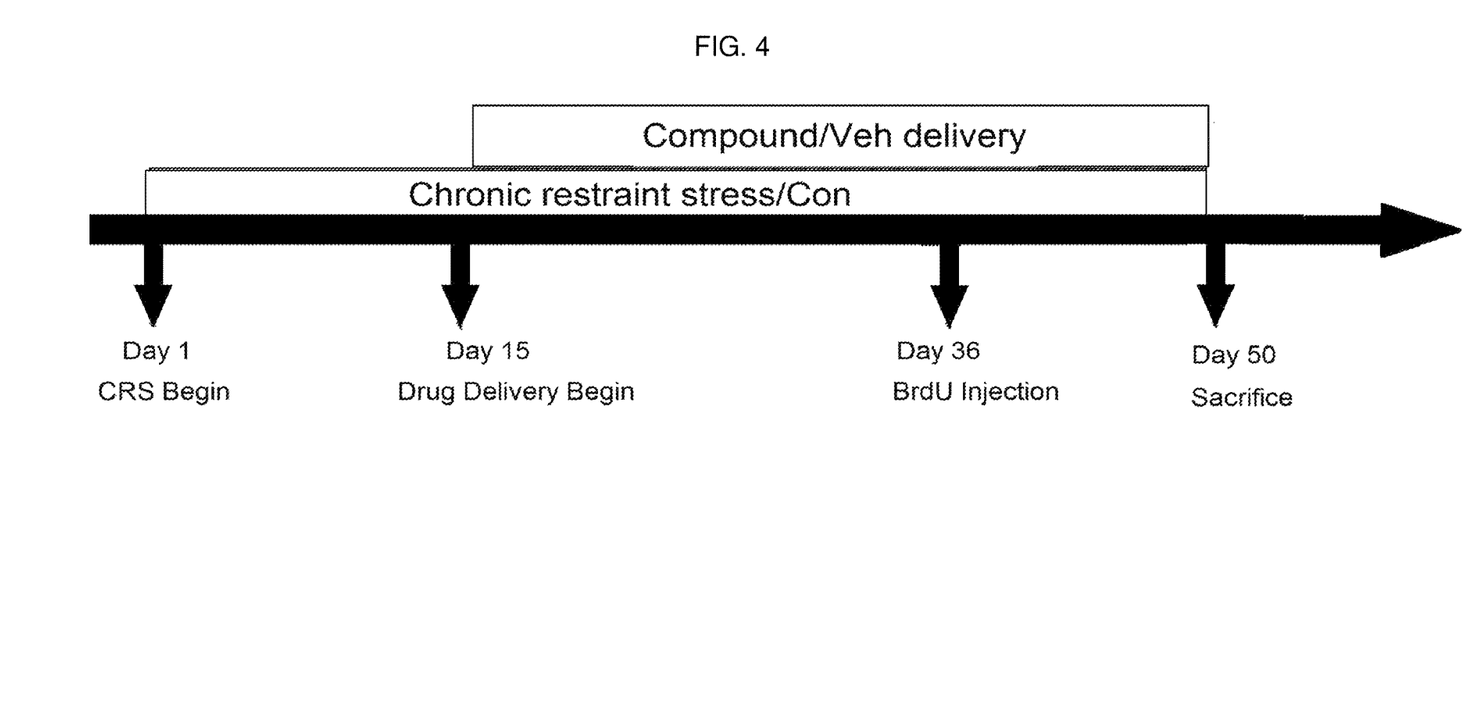
FIG. 4 is a chart showing the design of a 50-day trial to assess the effects of febuxostat on adult neurogenesis in the brains of mice subjected to chronic restraint stress.

Murine subjects underwent CRS on day zero, with febuxostat (1 mg kg$^{-1}$ d$^{-1}$) allopurinol (20 mg kg$^{-1}$ d$^{-1}$), Rhy37 (10 mg kg$^{-1}$ d$^{-1}$), or vehicle alone, administered daily intragastrically beginning on day 15. BrdU was administered on day 36, and brain tissues harvested on day 37 or 50. Control subjects remained free throughout the trial period. Neural progenitor amplification was measured by quantifying the number of BrdU-positive cells in hippocampal tissue sections. Neuronal differentiation was measured by quantifying doublecortin-positive (DCX+)/BrdU-positive cells in hippocampal tissue sections. Results were compared using a one-way ANOVA test. Experimental design is shown in FIGS. 2 and 4.

Figure 3:
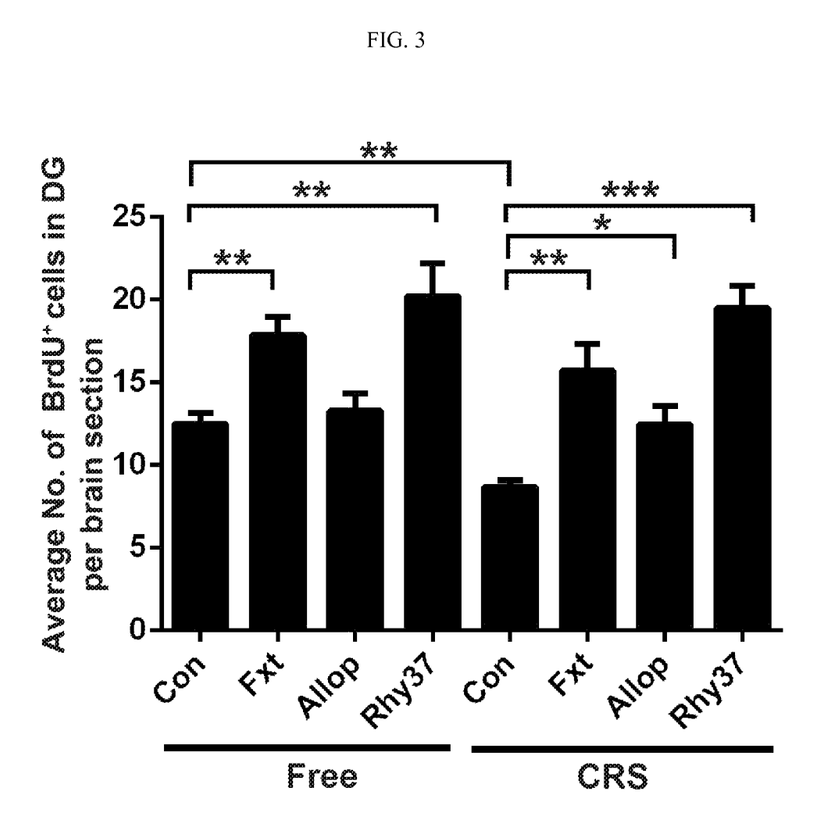
FIG. 3 is a chart showing that febuxostat promotes neuron progenitor amplification in the hippocampus of mice subjected to 37 days of chronic restraint stress, as compared to allopurinol or vehicle alone, and as compared to control animals not subject to restraint. Neural progenitor amplification was measured by BrdU incorporation. n=3 mice. All data are mean±SEM. **p<0.01, one-way ANOVA.
Figure 5:
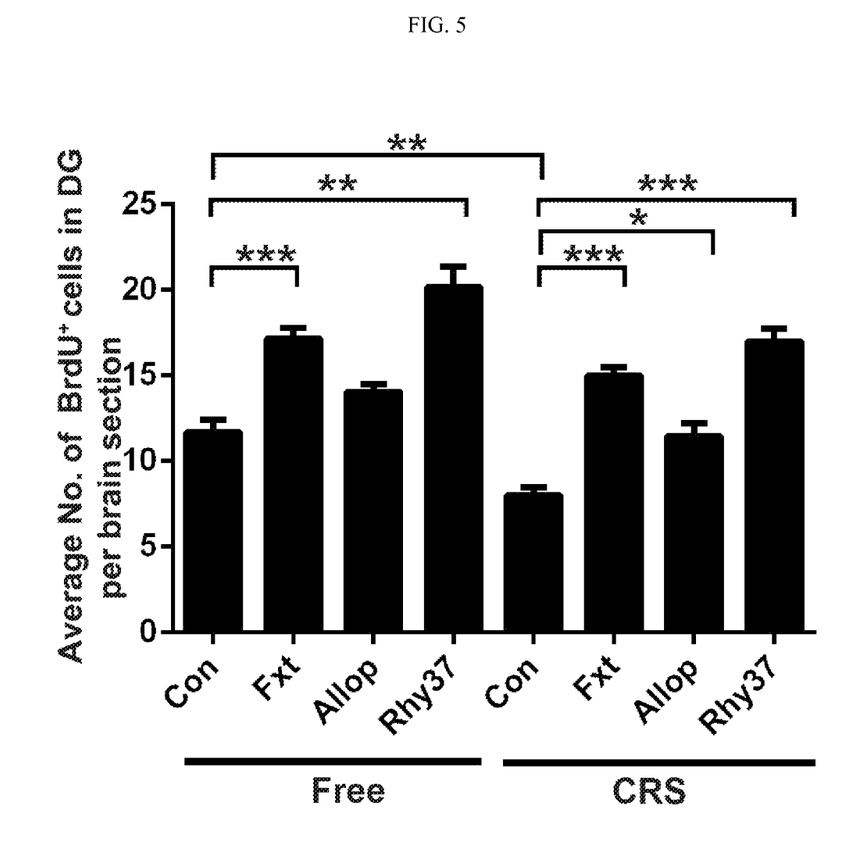
FIG. 5 is a chart showing that febuxostat promotes neuron progenitor amplification in the hippocampus of mice subjected to 50 days of chronic restraint stress, as compared to allopurinol or vehicle alone, and as compared to control animals not subject to restraint. Neural progenitor amplification was measured by BrdU incorporation. n=3 mice. All data are mean±SEM. **p<0.01, one-way ANOVA.
Figure 6:
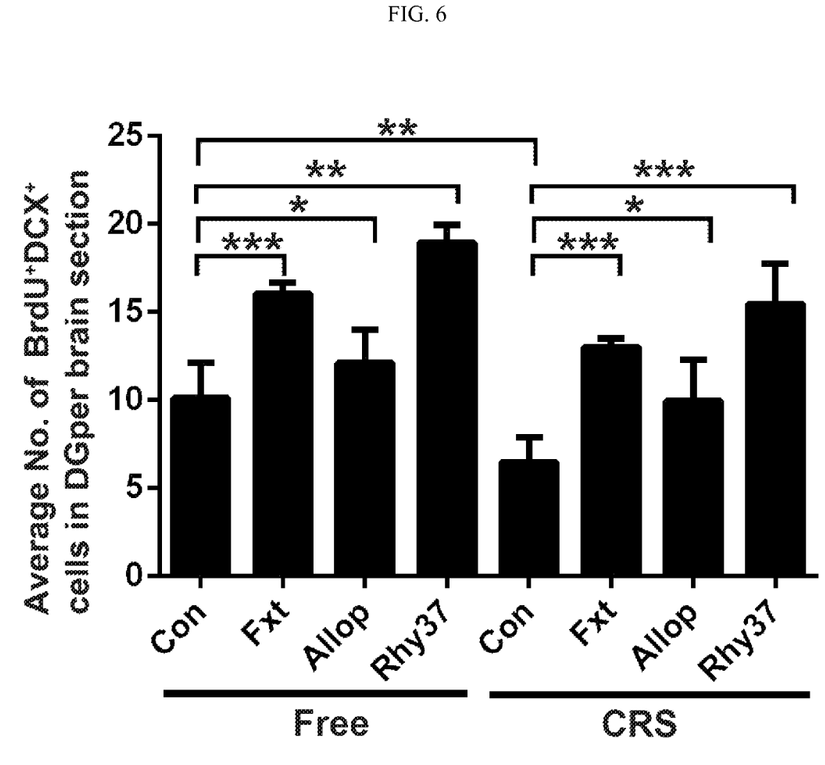
FIG. 6 is a chart showing that febuxostat promotes neuronal differentiation in the hippocampus of mice subjected to 50 days of chronic restraint stress, as compared to allopurinol or vehicle alone, and as compared to control animals not subject to restraint. Neuronal differentiation was measured by doublecortin (DCX) expression in conjunction with BrdU incorporation.

Results are shown in FIGS. 3, 5, and 6. Subjects receiving febuxostat or Rhy37 showed increased levels of neural progenitor amplification and neural differentiation compared to subjects receiving allopurinol or vehicle alone.

These results show that febuxostat is effective in methods for promoting adult neurogenesis and neural differentiation in mammalian subjects. Accordingly, febuxostat and febuxostat derivatives are effective for the treatment of disorders characterized by reduced neurogenesis or reduced neuron differentiation, or neuron loss, such as those described herein.

Example 3: Febuxostat Treatment of Psychiatric Disorders

This example will demonstrate that febuxostat and febuxostat derivatives are effective in the treatment of psychiatric disorders in human subjects, such as, but not limited to anxiety and depression.

Subjects suspected or diagnosed as having psychiatric disorders such as anxiety and depression will be administered one or more courses of febuxostat or febuxostat derivatives commensurate with the severity of disease and general condition of the subject. Following treatment, the subject will be evaluated clinically for improvement in the manifestations of the psychiatric disorder. For schizophrenia, suitable clinical endpoints include, but are not limited to: Positive and Negative Syndrome Scale (PANSS); the Brief Psychiatric Rating Scale derived (BPRSd), derived from the PANSS; and the Clinical Global Impression Improvement Scale (CGI-I); Clinical Assessment Interview for Negative Symptoms (CANS); Schizophrenia Outcomes Functioning Interview (SOFI); Brief Cognitive Assessment Tool for Schizophrenia (BCATS); UCSD Performance Based Skills Assessment-Brief Version (UPSA-B); Dysfunctional Attitudes Scale (DAS). For Anxiety/Mood disorders, suitable clinical endpoints include, but are not limited to: the Hamilton Scale for Anxiety (HAM-A); Anxiety Disorders Interview Schedule for DSM-IV-Lifetime Version (ADIS-IV); Mini or Superlite-ADIS-IV; Clinical Global Impression Severity (CGI-S) and Improvement Scales (CGI-I); SF-12 MCS; Structured Interview Guide for the Hamilton Anxiety and Depression Rating Scale (SIGH-A and SIGH-D); Yale-Brown Obsessive Compulsive Scale Interview (Y—BOCS); Panic Disorder Severity Scale (PDSS); Liebowitz Social Anxiety Scale (LSAS); Generalized Anxiety Disorder Severity Scale (GADSS); Post-Traumatic Stress Disorder (PTSD) Symptom Scale-Interview Version (PSS-I); Beck Depression Inventory (BDI-II); Beck Anxiety Inventory (BAI); Overall Anxiety Sensitivity and Impairment Scale (OASIS); Work and Social Adjustment Scale; Anxiety Sensitivity Index; Pediatric Anxiety Rating Scale (PARS). For Major Depressive Disorder (Depression) suitable clinical endpoints include, but are not limited to, the Montgomery-Asberg Depression Rating Scale (MADRS), a 10-item clinician-related scale used to assess the degree of depressive symptomatology, with 0 representing no symptoms, and 60 representing worst symptoms; The Hamilton Depression Scale (HAMD-24); Hamilton Anxiety Scale (HAM-A); The Sheehan Disability Scale (SDS); Sheehan Disability Scale (SDS); Clinical Global Impression-Severity scale (CGI-S); The Medical Outcomes Study SF-36 (36-item Short-form Health Survey). For Bipolar disorder suitable clinical endpoints include, but are not limited to: Young Mania Rating Scale (YMRS) and Clinical Global Impressions-Severity scale (CGI-S). For Attention Deficit Hyperactivity Disorder (ADHD) suitable clinical endpoints include, but are not limited to attention and behavior of the patients are evaluated using the SKAMP rating scale; The ADHD-Rating Scale I-IV.

It is predicted that subjects receiving one or more courses of febuxostat or febuxostat derivatives will display increased neural progenitor amplification and neural differentiation as compared to subjects not receiving febuxostat or febuxostat derivatives, and will show a decrease in the pathology of the psychiatric disorder and/or symptoms of the disorder. The results will show that febuxostat and febuxostat derivatives are effective for promoting adult neurogenesis, and for the treatment of psychiatric disorders such as anxiety and depression and related disorders.

Example 4: Febuxostat Treatment of Neurodegenerative Diseases

This example will demonstrate that febuxostat and febuxostat derivatives are effective in the treatment of neurodegenerative diseases in human subjects, such as, but not limited to Alzheimer's Disease (AD), Parkinson's Disease (PD), and amyotrophic lateral sclerosis (ALS).

Subjects suspected or diagnosed as having a neurodegenerative disease will be administered one or more courses of febuxostat or febuxostat derivatives commensurate with the severity of disease and general condition of the subject. Following treatment, the subject will be evaluated clinically for improvement in the manifestations of the disease. For Parkinson's Disease suitable clinical endpoints include, but are not limited to Unified Parkinson's Disease Rating Scale, parts I-IV (UPDRS-IV); Movement Disorder Society-Unified Parkinson's Disease Rating Scale (MDS-UPDRS I-IV); Parkinson's Disease Questionnaire-39 (PDQ-39), Patient Global Impression (PGI), Clinical Global Impression; Modified Schwab & England Independence Scale; Modified Rankin Scale; PD Quality of Life Scale; Symbol Digit Modalities Test; Hoehn & Yahr Score; Motor function ((characterized by UPDRS); Montreal Cognitive assessment Scale (MoCA); Global measures of disability as measured by modified Rankin score; Functional status and quality of life (Non-Motor Experience of Daily Living). For Alzheimer's Disease, suitable clinical endpoints include, but are not limited to: Time to diagnosis of MCI or dementia due to Alzheimer's Disease; Alzheimer's Prevention Initiative Composite Cognitive (APCC) Test Score; Clinical Dementia Rating Scale Sum of Boxes (CDR-SOB) score; Total Scale score and individual neurocognitive domain index scores of the RBANS; Everyday Cognition scale (ECog) total scores; Alzheimer's Disease Assessment Scale-Cognitive Subscale (ADAS-Cog-13) Score; Functional Activities Questionnaire (FAQ) Score; Alzheimer's Disease Cooperative Study Activities of Daily Living Inventory (ADCS-ADL) Instrumental Items Score; Neuropsychiatric Inventory (NPI) Score; Concentration of Cerebrospinal fluid (CSF) Biomarker Aβ1-42; Concentration of CSF Biomarker Aβ1-40; Amyloid Imaging Positron Emission Tomography (AV-45 PET); Cerebral Spinal Fluid (CSF) Total Tau; Magnetic Resonance Imaging (MRI) brain volumetric measures. For ALS suitable clinical endpoints include, but are not limited to: Amyotrophic Lateral Sclerosis functional rating scale (ALSFRS-Revised); Overall survival (OS); Forced vital capacity (FVC); Time to death or death equivalent (tracheostomy or permanent assisted ventilation (PAV); Amyotrophic Lateral Sclerosis Assessment Questionnaire-5-Item Form (ALSAQ-5).

It is predicted that subjects receiving one or more courses of febuxostat or febuxostat derivatives will display increased neural progenitor amplification and neural differentiation as compared to subjects not receiving febuxostat or febuxostat derivatives, and will show a decrease in the pathology of the neurodegenerative disease and/or symptoms of the disease. The results will show that febuxostat and febuxostat derivatives are effective for promoting adult neurogenesis, and for the treatment of neurodegenerative diseases such as Alzheimer's Disease (AD), Parkinson's Disease (PD), and amyotrophic lateral sclerosis (ALS), and related disorders.

Example 5: Febuxostat Treatment of Age-Related Neuron Loss

This example will demonstrate that febuxostat and febuxostat derivatives are effective in the treatment of age-related neuron loss in human subjects.

Subjects suspected or diagnosed as having age-related neuron loss will be administered one or more courses of febuxostat or febuxostat derivatives commensurate with the severity of disease and general condition of the subject. Following treatment, the subject will be evaluated clinically for improvement in the manifestations of the condition. Suitable clinical endpoints include but are not limited to: measurement of brain activity during task performance and measurement of change in regional brain volumes; recognition memory tests during and after functional MRI; Total Hippocampal Volume (HCV); COWAT: Verbal fluency test; Mini Mental State Examination (MMSE) Total Score;

It is predicted that subjects receiving one or more courses of febuxostat or febuxostat derivatives will display increased neural progenitor amplification and neural differentiation as compared to subjects not receiving febuxostat or febuxostat derivatives, and will show a decrease in the pathology of age-related neuron loss and/or symptoms of the condition. The results will show that febuxostat and febuxostat derivatives are effective for promoting adult neurogenesis, and for the treatment of age-related neuron loss and related disorders.

Example 6: Febuxostat Treatment of Noise-Induced Hearing Loss

This example will demonstrate that febuxostat and febuxostat derivatives are effective in the treatment of noise-induced hearing loss in human subjects.

Subjects suspected or diagnosed as having noise-induced hearing loss will be administered one or more courses of febuxostat or febuxostat derivatives commensurate with the severity of disease and general condition of the subject. Following treatment, the subject will be evaluated clinically for improvement in the manifestations of the condition. Suitable clinical endpoints include, but are not limited to: Sensory thresholds at pure tone frequencies (typically from 0.125 KHz through 16 KHz); otoacoustic emission (OAE) testing; brainstem auditory evoked responses (BAER); assessments of the vestibular organs for clinically relevant functional improvement; speech recognition improvement (word and/or sentence); distortion-product otoacoustic emissions (DPOAE); time to recovery following acute noise exposure.

It is predicted that subjects receiving one or more courses of febuxostat or febuxostat derivatives will display increased neural progenitor amplification and neural differentiation as compared to subjects not receiving febuxostat or febuxostat derivatives, and will show a decrease in the pathology of noise-induced hearing loss and/or symptoms of the condition. The results will show that febuxostat and febuxostat derivatives are effective for promoting adult neurogenesis, and for the treatment of noise-induced hearing loss and related disorders.

Example 6: Febuxostat Treatment of Tardive Dyskinesia

This example will demonstrate that febuxostat and febuxostat derivatives are effective in the treatment of tardive dyskinesia in human subjects.

Subjects suspected or diagnosed as having tardive dyskinesia will be administered one or more courses of febuxostat or febuxostat derivatives commensurate with the severity of disease and general condition of the subject. Following treatment, the subject will be evaluated clinically for improvement in the manifestations of the condition. Suitable clinical endpoints include, but are not limited to: abnormal Involuntary Movement Scale (AIMS); Clinical Global Impression of Change TD (CGIC-TD); Patient Global Impression of Change (PGIC) questionnaire; Tardive Dyskinesia Impact Scale (TDIS); Barnes Akathisia Scale; Extrapyramidal Symptom Rating Scale (ESRS).

It is predicted that subjects receiving one or more courses of febuxostat or febuxostat derivatives will display increased neural progenitor amplification and neural differentiation as compared to subjects not receiving febuxostat or febuxostat derivatives, and will show a decrease in the pathology of tardive dyskinesia and/or symptoms of the subject. The results will show that febuxostat and febuxostat derivatives are effective for promoting adult neurogenesis, and for the treatment of tardive dyskinesia and related disorders.

The invention claimed is:

1. A method for promoting adult neurogenesis in a subject in need thereof, comprising administering to the subject a composition comprising febuxostat, wherein the febuxostat promotes neuronal progenitor amplification and neuronal differentiation.

2. The method of claim 1, wherein the subject is suspected or diagnosed as having a psychiatric disorder, noise-induced hearing loss, age-related neuron loss, tardive dyskinesia, or a neurodegenerative condition.

3. The method of claim 2, wherein the psychiatric disorder is selected from the group consisting of anxiety and depression.

4. The method of claim 2, wherein the neurodegenerative condition is selected from the group consisting of Alzheimer's Disease (AD), Parkinson's Disease (PD), and amyotrophic lateral sclerosis (ALS).

5. The method of claim 1, wherein the febuxostat promotes an increase in the number of doublecortin-positive (DCX$^+$) cells in the subject's hippocampal region.

6. The method of claim 1, further comprising administering one or more additional agents for promoting adult neurogenesis.

* * * * *